(12) United States Patent
Yamashina et al.

(10) Patent No.: US 6,881,190 B2
(45) Date of Patent: Apr. 19, 2005

(54) STANDARD PULSE-WAVE-PROPAGATION-VELOCITY-RELATED-VALUE DETERMINING APPARATUS AND PULSE-WAVE-PROPAGATION-VELOCITY-RELATED-VALUE OBTAINING APPARATUS

(75) Inventors: Akira Yamashina, Bunkyo-ku (JP);
Hideichi Tsuda, Komaki (JP)

(73) Assignee: Colin Medical Technology Corporation, Komaki (JP)

( * ) Notice: Subject to any disclaimer, the term of this patent is extended or adjusted under 35 U.S.C. 154(b) by 74 days.

(21) Appl. No.: 10/356,475

(22) Filed: Feb. 3, 2003

(65) Prior Publication Data

US 2003/0167011 A1 Sep. 4, 2003

(30) Foreign Application Priority Data

Mar. 1, 2002 (JP) ..................... 2002-056198

(51) Int. Cl.$^7$ ............................. A61B 5/02
(52) U.S. Cl. ............... 600/481; 600/485; 600/500; 600/504
(58) Field of Search ............... 600/300, 301, 600/481, 485–508

(56) References Cited

U.S. PATENT DOCUMENTS

| | | | | |
|---|---|---|---|---|
| 4,779,619 A | * | 10/1988 | Winkler | 600/410 |
| 5,103,833 A | * | 4/1992 | Apple | 600/500 |
| 5,343,867 A | * | 9/1994 | Shankar | 600/481 |
| 5,638,823 A | * | 6/1997 | Akay et al. | 600/528 |
| 5,711,303 A | * | 1/1998 | Shimizu et al. | 600/490 |
| 5,743,856 A | | 4/1998 | Oka et al. | |
| 5,776,071 A | * | 7/1998 | Inukai et al. | 600/493 |
| 6,379,309 B1 | | 4/2002 | Ogura et al. | |

FOREIGN PATENT DOCUMENTS

| | | |
|---|---|---|
| DE | 198 18 147 C1 | 11/1999 |
| DE | 199 60 425 A1 | 8/2001 |
| JP | A 9-122091 | 5/1997 |
| JP | 2001-190506 A | 7/2001 |
| WO | WO 00/76394 A1 | 12/2000 |

OTHER PUBLICATIONS

Franchi D et al. "Blood Pressure Evaluation Based on Arterial Pulse Wave Velocity" *Computers in Cardiology;* 397–400: 9(1996).

* cited by examiner

*Primary Examiner*—Max F. Hindenburg
*Assistant Examiner*—Patricia Mallari
(74) *Attorney, Agent, or Firm*—Oliff & Berridge, PLC (57) ABSTRACT

An apparatus for determining a standard pulse-wave-propagation-velocity-related value for a living subject, comprising: a blood-pressure measuring device for measuring a blood pressure of the subject; an age determining device for determining an age of the subject; and a standard-pulse-wave-propagation-velocity-related-value determining device for determining the standard pulse-wave-propagation-velocity-related value for the subject, based on the blood pressure of the subject measured by the blood-pressure measuring device and the age of the subject determined by the age determining device, according to a predetermined relationship between (A) (a1) blood pressure and (a2) age and (B) standard pulse-wave-propagation-velocity-related value.

7 Claims, 5 Drawing Sheets

STANDARD PULSE-WAVE-PROPAGATION-VELOCITY-RELATED-VALUE DETERMINING APPARATUS AND PULSE-WAVE-PROPAGATION-VELOCITY-RELATED-VALUE OBTAINING APPARATUS

BACKGROUND OF THE INVENTION

1. Field of the Invention

The present invention relates to the art of determining a standard pulse-wave-propagation-velocity-related value for a living subject.

2. Related Art Statement

The pulse-wave-propagation-velocity-related information which is related to a velocity at which a pulse wave propagates in a living subject includes a pulse-wave propagation velocity, and a pulse-wave propagation time, for instance. A standard value of the pulse-wave-propagation-velocity-related information is obtained from a normal subject who is free from arteriosclerosis.

Arteriosclerosis is known as a factor that influences the pulse-wave-propagation-velocity-related information. This is utilized to evaluate a degree of arteriosclerosis of a living subject, i.e., the hardness of an artery of the subject. For instance, JP-A-9-122091 or its corresponding U.S. Pat. No. 5,743,856 discloses an apparatus for obtaining a pulse-wave propagation velocity to evaluate the hardness of the artery of the subject.

In a case where the obtained value of the pulse-wave-propagation-related information largely deviates from the standard value of the pulse-wave-propagation-velocity-related information, a medical treatment such as administration of drug is conducted on the subject or the subject is advised to change his/or her life habit in order to lower or reduce the degree of arteriosclerosis. Further, it can also be judged, from the pulse-wave-propagation-velocity-related value, to what extent the degree of arteriosclerosis is lowered owing to the administration of drug or the change of the life habit.

The standard pulse-wave-propagation-velocity-related value is not always constant, but varies depending upon blood pressure, age, etc., of a living subject. Therefore, it is not easy to determine the standard pulse-wave-propagation-velocity-related value. Further, it is not easy to judge to what extent the obtained pulse-wave-propagation-velocity-related value deviates from the standard pulse-wave-propagation-velocity-related value. In a case where the degree of arteriosclerosis is judged, the standard pulse-wave-propagation-velocity-related value determined in a present diagnosis tends to differ from that determined in a previous diagnosis conducted prior to the present diagnosis since the blood pressure measured in the present diagnosis is usually not the same as that measured in the previous diagnosis. Accordingly, it is difficult to judge whether or not the pulse-wave-propagation-velocity-related-value obtained in the present diagnosis deviates from the standard pulse-wave-propagation-velocity-related value, that is, whether or not the degree of arteriosclerosis is lowered.

SUMMARY OF THE INVENTION

It is therefore an object of the present invention to provide a standard-pulse-wave-propagation-velocity-related-value determining apparatus which can accurately determine a standard pulse-wave-propagation-velocity-related-value for a living subject.

The above object may be achieved according to a principle of the present invention, which provides an apparatus for determining a standard pulse-wave-propagation-velocity-related value for a living subject, comprising: a blood-pressure measuring device for measuring a blood pressure of the subject; an age determining means for determining an age of the subject; and a standard-pulse-wave-propagation-velocity-related-value determining means for determining the standard pulse-wave-propagation-velocity-related value for the subject, based on the blood pressure of the subject measured by the blood-pressure measuring device and the age of the subject determined by the age determining means, according to a predetermined relationship between (A) (a1) blood pressure and (a2) age and (B) standard pulse-wave-propagation-velocity-related value.

According to this invention, the relationship between (A) (a1) blood pressure and (a2) age and (B) standard pulse-wave-propagation-velocity-related-value is predetermined. The standard-pulse-wave-propagation-velocity-related-value determining means determines the standard pulse-wave-propagation-velocity-related value for the subject, based on the blood pressure and the age of the subject, according to the predetermined relationship. Thus, an accurate standard pulse-wave-propagation-related value can be determined for the subject.

In one preferred form of the invention, the apparatus further comprises a gender determining means for determining a gender of the subject, wherein the predetermined relationship between (A)(a1) blood pressure and (a2) age and (B) standard pulse-wave-propagation-velocity-related value comprises two predetermined relationships between (A)(a1) blood pressure and (a2) age and (B) standard pulse-wave-propagation-velocity-related value that correspond to male and female, respectively, and wherein the standard-pulse-wave-propagation-velocity-related-value determining means determines the standard pulse-wave-propagation-velocity-related value for the subject, according to one of the two predetermined relationships between (A)(a1) blood pressure and (a2) age and (B) standard pulse-wave-propagation-velocity-related value that corresponds to the gender of the subject determined by the gender determining means. According to this form of the invention, the standard pulse-wave-propagation-velocity-related value for the subject is determined by taking into account not only the blood pressure and the age of the subject, but also the gender of the subject. Thus, a more accurate standard pulse-wave-propagation-velocity-related value can be determined for the subject.

The standard pulse-wave-propagation-velocity-related-value determining apparatus described above may be incorporated into an apparatus for obtaining a pulse-wave-propagation-velocity-related value of a living subject which includes a measuring device for measuring an actual pulse-wave-propagation-velocity-related value of a living subject. That is, the pulse-wave-propagation-velocity-related value obtaining apparatus comprises: the above-described standard-pulse-wave-propagation-velocity-related-value determining apparatus; an actual-pulse-wave-propagation-velocity-related-value measuring device for measuring an actual pulse-wave-propagation-velocity-related value that is related to a velocity at which a pulse wave propagates in the subject; and a display device which displays the standard pulse-wave-propagation-velocity-related value determined by the standard-pulse-wave-propagation-velocity-related-value determining apparatus and the actual pulse-wave-propagation-velocity-related value measured by the actualpulse-wave-propagation-velocity-related-value measuring device. According to the invention wherein both of the standard pulse-wave-propagation-velocity-related value and the actual pulse-wave-propagation-velocity-related value are displayed by the display device, the degree of arteriosclerosis can be easily judged by comparing the standard pulse-wave-propagation-velocity-related value and the actual pulse-wave-propagation-velocity-related value with each other In another preferred form of the invention, the actual-pulse-wave-propagation-velocity-related-value measuring device comprises: an upper-arm-pulse-wave detecting device which includes an upper-arm cuff adapted to be wound around an upper arm of the subject and detects an upper-arm pulse wave of the subject; an ankle-pulse-wave detecting device which includes an ankle cuff adapted to be wound around an ankle of the subject and detects an ankle pulse wave of the subject; and means for determining the actual pulse-wave-propagation-velocity-related value of the subject, based on the upper-arm pulse wave detected by the upper-arm-pulse-wave detecting device and the ankle pulse wave detected by the ankle-pulse-wave detecting device.

In still another preferred form of the invention, the actual-pulse-wave-propagation-velocity-related-value measuring device comprises an actual-pulse-wave-propagation-time determining means for determining an actual pulse-wave-propagation time as a time difference between a time of detection of a prescribed point of the upper-arm pulse wave and a time of detection of a corresponding prescribed point of the ankle pulse wave.

In yet another preferred form of the invention, the actual-pulse-wave-propagation-velocity-related-value measuring device further comprises an actual-pulse-wave-propagation-velocity determining means for determining an actual pulse-wave-propagation velocity at which the pulse wave propagates, by dividing a propagation distance which is a difference between a distance between an aortic valve of the heart of the subject and a portion of the upper arm around which the upper-arm cuff is wound, and a distance between the aortic valve of the heart of the subject and a portion of the ankle around which the ankle cuff is wound, by the actual pulse-wave-propagation time determined by the actual-pulse-wave-propagation-time determining means.

In a further preferred form of the invention, the standard pulse-wave-propagation-velocity-related-value determining apparatus further comprises an input device operable for inputting the age of the subject, wherein the age determining means determines, as the age of the subject, the age inputted through the input device.

In a yet further preferred form of the invention, the standard pulse-wave-propagation-velocity-related-value determining apparatus further comprises an input device operable for inputting the gender of the subject, wherein the gender determining means determines, as the gender of the subject, the gender inputted through the input device.

BRIEF DESCRIPTION OF THE DRAWINGS

The above and optional objects, features, and advantages of the present invention will be better understood by reading the following detailed description of preferred embodiments of the invention when considered in conjunction with the accompanying drawings, in which.

DETAILED DESCRIPTION OF PREFERRED EMBODIMENTS

Figure 1:
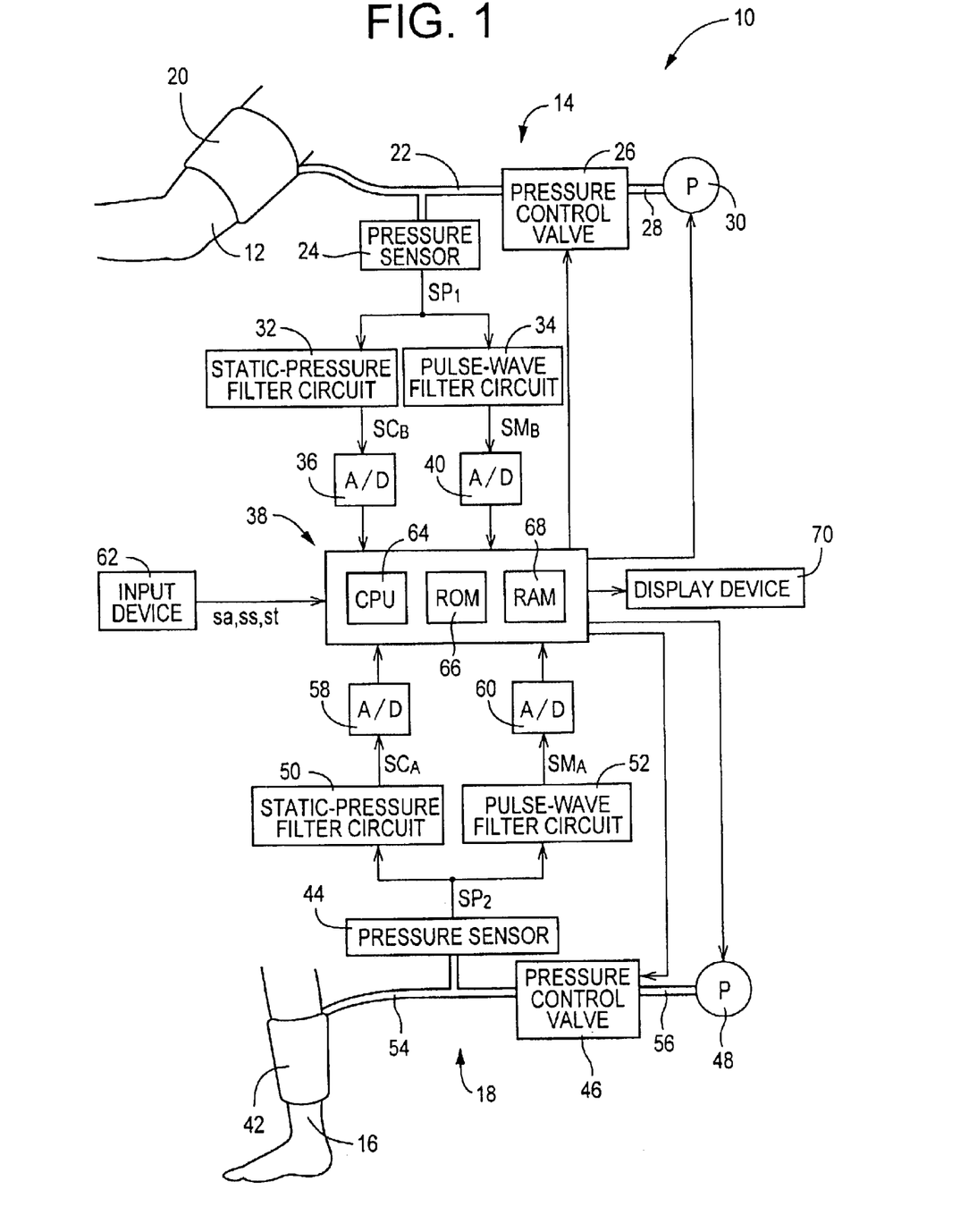
FIG. 1 is a diagrammatic view for explaining a construction of a pulse-wave-propagation-velocity-related-value obtaining apparatus to which the present invention is applied.

Hereinafter, there will be described preferred embodiments of the present invention in detail by reference to the drawings. FIG. 1 is a diagrammatic view for explaining a construction of a pulse-wave-propagation-velocity-related-value obtaining apparatus 10 to which the present invention is applied.

The pulse-wave-propagation-velocity-related-value obtaining apparatus 10 includes an upper-arm-pulse-wave detecting device 14 which detects a pulse wave from an upper arm 12 of a living subject, i.e., an upper-arm pulse wave wb, and an ankle-pulse-wave detecting device 18 which detects a pulse wave from an ankle 16 of the subject, i.e., an ankle pulse wave wa. The upper-arm-pulse-wave detecting device 14 also functions as an upper-arm blood pressure (BP) measuring device for measuring a blood pressure in the upper arm 12 of the subject.

The upper-arm-pulse-wave detecting device 14 includes: an upper-arm cuff 20 which includes a belt-like cloth bag and a rubber bag accommodated in the cloth bag and which is adapted to be wound around the upper arm 12 of the subject; a piping 22; a pressure sensor 24; and a pressure control valve 26. The pressure sensor 24 and the pressure control valve 26 are connected to the upper-arm cuff 20 via the piping 22. An air pump 30 is connected to the pressure control valve 26 via a piping 28. The pressure control valve 26 adjusts a pressure of a pressurized air supplied from the air pump 30, and supplies the pressure-adjusted air to the upper-arm cuff 20, or discharges the pressurized air from the upper-arm cuff 20, so as to control an air pressure in the upper-arm cuff 20.

The pressure sensor 24 detects the air pressure in the upper-arm cuff 20, and supplies a pressure signal, SP1, representing the detected air pressure, to a static-pressure filter circuit 32 and a pulse-wave filter circuit 34. The static-pressure filter circuit 32 includes a low-pass filter which extracts, from the pressure signal SP1, an upper-arm-cuff-pressure signal $SC_B$, representing a static component of the detected air pressure, i.e., a pressing pressure of the upper-arm cuff 20 (hereinafter, referred to as the upper-arm-cuff pressure $PC_B$). The filter circuit 32 supplies the upper-arm-cuff-pressure signal $SC_B$ to an electronic control device 38 via an A/D (analog-to-digital) converter 36.

The pulse-wave filter circuit 34 includes a band-pass filter which extracts, from the pressure signal SP1, an upper-arm-pulse-wave signal, $SM_B$, representing an upper-arm pulse wave as an oscillatory component of the detected air pressure that has prescribed frequencies. The filter circuit 34 supplies the upper-arm-pulse-wave signal $SM_B$ to the control device 38 via an A/D converter 40. The upper-arm-pulse-wave signal $SM_B$ represents the upper-arm pulse wave wb.

The ankle-pulse-wave detecting device 18 includes: an ankle cuff 42; a pressure sensor 44; a pressure control valve 46; an air pump 48; a static-pressure filter circuit 50; and a pulse-wave filter circuit 52, which have respective constructions identical with those of the counterparts of the upper-arm-pulse-wave detecting device 14. The ankle cuff 42, the pressure sensor 44, and the pressure control valve 46 are connected to one another via a piping 54. The pressure control valve 46 and the air pump 48 are connected to each other via a piping 56. The pressure sensor 44 detects an air pressure in the ankle cuff 42, and supplies a pressure signal SP2, representing the detected air pressure, to the static-pressure filter circuit 50 and the pulse-wave filter circuit 52. The static-pressure filter circuit 50 extracts, from the pressure signal SP2, an ankle-cuff-pressure signal $SC_A$, representing a static component of the detected air pressure, i.e., a pressing pressure of the ankle cuff 42 (hereinafter, referred to as the ankle-cuff pressure, $PC_A$). The filter circuit 50 supplies the ankle-cuff-pressure signal $SC_A$ to the control device 38 via an A/D converter 58. The pulse-wave filter circuit 52 extracts, from the pressure signal SP2, an ankle-pulse-wave signal $SM_A$, representing an ankle pulse wave as an oscillatory component of the detected air pressure that has prescribed frequencies. The filter circuit 52 supplies the ankle-pulse-wave signal $SM_A$ to the control device 36 via an A/D converter 60. The ankle-pulse-wave-signal $SM_A$ represents the ankle pulse wave wa.

An input device 62 includes a plurality of keys, not shown, which are operated by an operator such as a doctor or a nurse to input an age a, a gender s, and a stature t, of the subject. The input device 62 supplies, to the control device 38, an age signal sa, a gender signal ss, and a stature signal st which represent the inputted patient's age a, gender s, and stature t, respectively.

The control device 38 is essentially provided by a microcomputer including a CPU (central processing unit) 64, a ROM (read only memory) 66, a RAM (random access memory) 68, and an I/O (input-and-output) port, not shown, and the CPU 64 processes signals according to the programs pre-stored in the ROM 66, while utilizing the data-storing function of the RAM 68. The control device 38 outputs, from the I/O port, drive signals to the two air pumps 30, 48 and the two pressure control valves 26, 46 so as to control the respective operations thereof and thereby control the upper-arm cuff pressure $PC_B$ and the ankle cuff pressure $PC_A$. In addition, the CPU 64 processes signals supplied to the control device 38, so as to determine a standard pulse-wave-propagation-velocity-related vale and an actual pulse-wave-propagation-velocity-related value, and control a display device 70 to display the thus determined standard pulse-wave-propagation-velocity-related value and the actual pulse-wave-propagation-velocity-related value.

Figure 2:
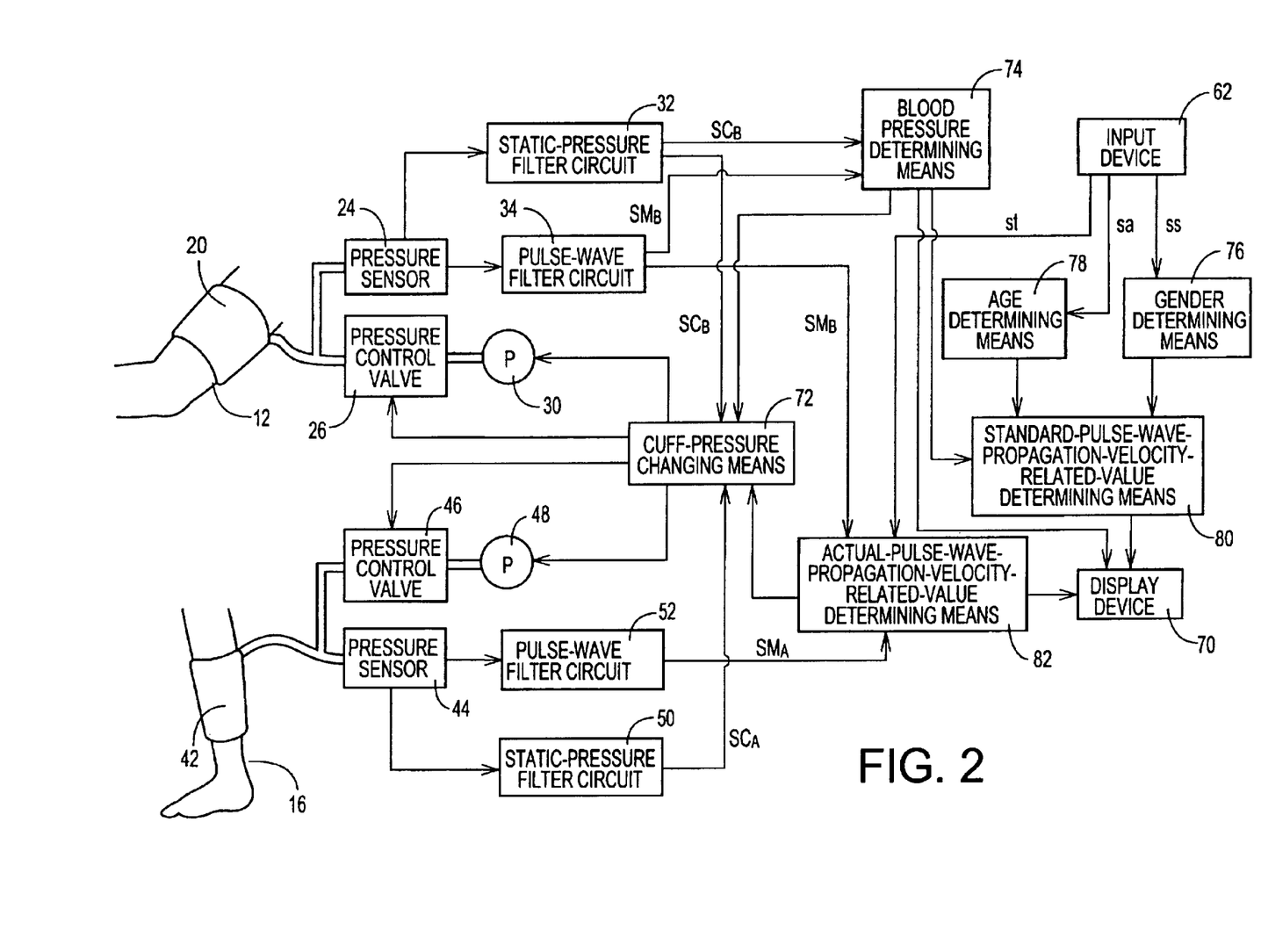
FIG. 2 is a diagrammatic view for explaining essential control functions of an electronic control device of the apparatus of FIG. 1.

FIG. 2 is a diagrammatic view for explaining essential control functions of the electronic control device 38. A cuff-pressure changing means 72 is operated according to a command signal supplied from a blood-pressure (BP) determining means 74 described later, so as to control the air pump 30 and the pressure control valve 26 connected to the pump 30, based on the upper-arm-cuff-pressure signal $SC_B$ supplied from the static-pressure filter circuit 32, and thereby control the upper-arm cuff pressure $PC_B$ as follows: First, the upper-arm cuff pressure $PC_B$ is quickly increased to a pre-set target pressure $PC_{M2}$ (e.g., 180 mmHg). Then, the upper-arm cuff pressure $PC_B$ is slowly decreased at a rate of, e.g., 3 mmHg/sec. In addition, after a blood pressure $BP_{DIA}$ is determined by the BP determining means 74, the upper-arm cuff pressure $PC_B$ is decreased to an atmospheric pressure.

In addition, the cuff-pressure changing means 72 is operated according to a command signal supplied from an actual pulse-wave-propagation-velocity-related-value-determining means 82 described later, so as to control the two air pumps 30, 48 and the two pressure control valves 26, 46 respectively connected to the air pumps 30, 48, based on the upper-arm-cuff-pressure signal $SC_B$ and the ankle-cuff-pressure signal $SC_A$ supplied from the static-pressure filter circuits 32, 50, and thereby change, and keep, the upper-arm cuff pressure $PC_B$ and the ankle cuff pressure $PC_A$ to, and at, respective pre-set pulse-wave detecting pressures. The pulse-wave detecting pressures are expected to be lower than the diastolic blood pressure values of the body portions of the subject around which the cuffs 20, 42 are respectively wound, but permit the pulse-wave signals SM extracted by the pulse-wave filter circuits 34, 52 to have a sufficiently high degree of signal strength. The pulse-wave detecting pressures are pre-set to 50 mmHg, for instance.

The blood-pressure determining means 74 obtains, during the slow decreasing of the upper-arm cuff pressure $PC_B$ under the control of the cuff-pressure changing means 72, the upper-arm cuff pressure $PC_B$ and a variation of respective amplitudes of pulses of the upper-arm pulse wave wb, based on the upper-arm-cuff-pressure signal $SC_B$ and the upper-arm-pulse-wave signal $SM_B$ continuously supplied from the static-pressure filter circuit 32 and the pulse-wave filter circuit 34, respectively, and determines, according to a well-known oscillometric algorithm, a systolic blood pressure value $BP_{SYS}$, a diastolic blood pressure value $BP_{DIA}$, and a mean blood pressure value $BP_{MEAN}$ of the upper arm 12, based on the obtained upper-arm cuff pressure $PC_B$ and the variation of the respective amplitudes of the pulses of the upper-arm pulse wave wb.

The gender determining means 76 determines the gender s of the subject based on the gender signal ss inputted through the input device 62. The age determining means 78 determines the age a of the subject based on the age signal sa inputted through the input device 62.

The standard pulse-wave-propagation-velocity-related value determining means 80 determines a standard pulse-wave-propagation-velocity-related value for the subject, based on the gender s determined by the gender determining means 76, the age a determined by the age determining means 78, and the blood pressure BP determined by the BP determining means 74, according to a predetermined relationship between (A) (a1) blood pressure and (a2) age and (B) standard pulse-wave-propagation-velocity-related value, which relationship is pre-stored in the ROM 66. The determined standard pulse-wave-propagation-velocity-related value is displayed by the display device 70. (This predetermined relationship is hereinafter referred to as "standard-value-determine relationship.) The standard-value-determine relationship is utilized for determining the standard pulse-wave-propagation-velocity-related value for the subject, based on the gender s, the age a, and the blood pressure BP of the subject, and is predetermined based on a multiplicity of relationships between (A) (a1) blood pressure and (a2) age and (B) pulse-wave-propagation-velocity-related value which were actually obtained from a multiplicity of normal male subjects and normal female subjects who are free from arteriosclerosis. Any one of the systolic blood pressure value $BP_{SYS}$, mean blood pressure value $BP_{MEAN}$, and diastolic blood pressure value $BP_{DIA}$ may be used in the standard-value-determine relationship. It is, however, preferable to employ the systolic blood pressure value $BP_{SYS}$ which is most relevant to the arteriosclerosis.

Figure 3A:
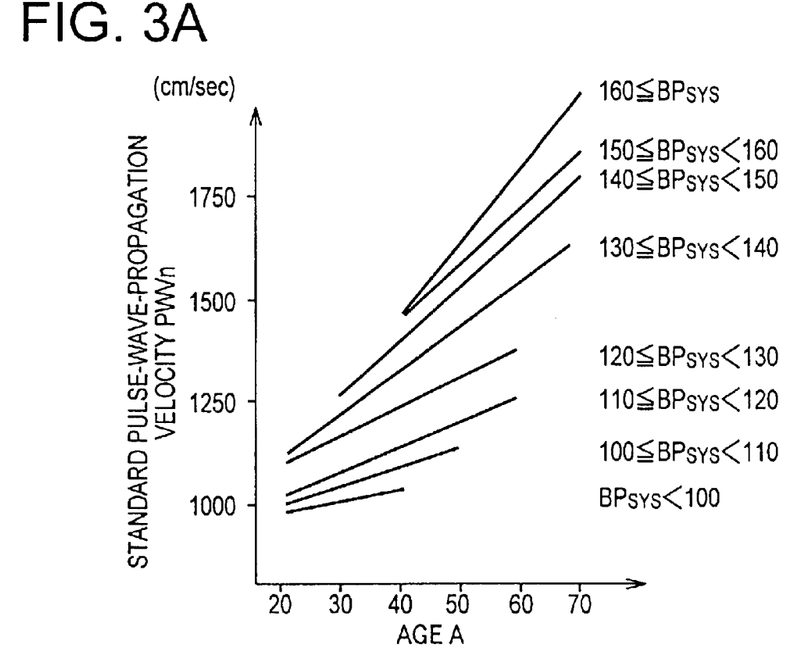
FIGS. 3A and 3B are graphical representations of two predetermined relationships used by a standard-pulse-wave-propagation-velocity-related-value determining means shown in FIG. 2.
Figure 3B:
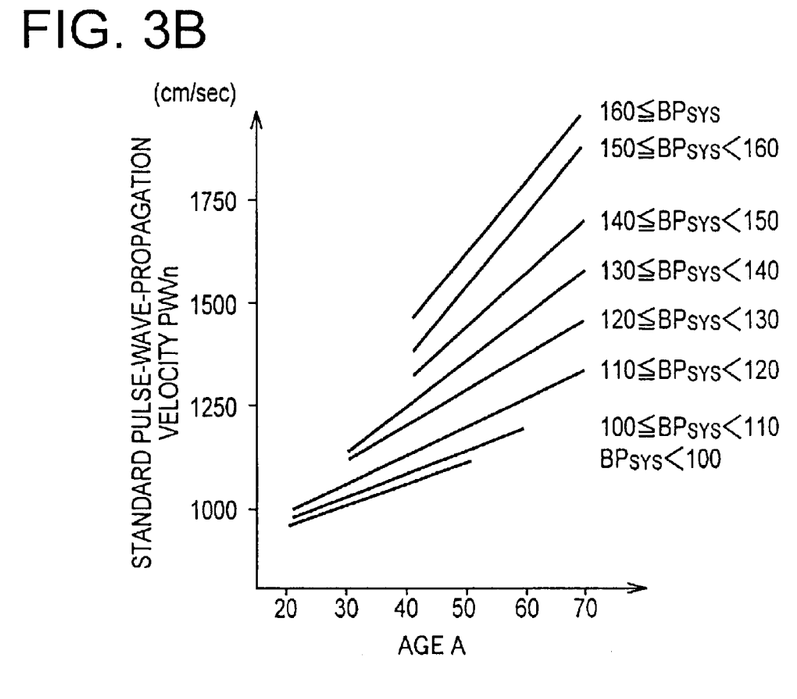

FIGS. 3A and 3B are graphical representations of the standard-value-determine relationship wherein a standard pulse-wave-propagation velocity PWVn is used as the standard pulse-wave-propagation-velocity-related value. The graph of FIG. 3A represents the standard pulse-wave-propagation-velocity-determine relationship for male while the graph of FIG. 3B represents the standard-pulse-wave-propagation-velocity-determine relationship for female. Each of the standard-pulse-wave-propagation-velocity-determine relationships represented by the respective graphs of FIGS. 3A and 3B comprises a plurality of relationships (represented by respective straight lines) between (A) (a2) age and (B) standard pulse-wave-propagation velocity. Described in detail, the plurality of relationships represented by the respective straight lines are predetermined so as to correspond to the systolic blood-pressure $BP_{SYS}$ in a predetermined range, e.g., 100–160 mmHg. Each of the plurality of relationships is predetermined for every 10 mmHg in the range of the systolic blood pressure $BP_{SYS}$. The plurality of relationships represented by the respective straight lines in the graphs of FIGS. 3A and 3B are stored in the ROM 66 in the form of respective linear expressions of first order.

The actual-pulse-wave-propagation-velocity-related-value determining means 82 determines an actual pulse-wave-propagation-velocity-related value of the subject, based on the upper-arm pulse wave wb and the ankle pulse wave wa which are respectively detected by the upper-arm-pulse-wave detecting device 14 and the ankle-pulse-wave detecting device 18 while the upper-arm cuff pressure $PC_B$ and the ankle cuff pressure $PC_A$ are kept at the respective pre-determined pulse-wave detecting pressures by the cuff-pressure changing means 72. Described in detail, the actual-pulse-wave-propagation-velocity-related-value determining means 82 determines, as an actual pulse-wave-propagation time DTa (sec), a time difference between a time of detection of a prescribed point (e.g., a rising point or a peak point) of the upper-arm pulse wave wb detected by the upper-arm-pulse-wave detecting device 14 while the upper-arm cuff pressure $PC_B$ is kept at the predetermined pulse-wave detecting pressure, and a time of detection of a corresponding prescribed point of the ankle pulse wave wa detected by the ankle-pulse-wave-detecting device 18 while the ankle cuff pressure $PC_A$ is kept at the predetermined pulse-wave detecting pressure.

Moreover, the actual pulse-wave-propagation-related-value determining means 82 substitutes the subject's stature t represented by the stature signal st supplied from the input device 76, with the following Expression 1 which represents a relationship between stature t and propagation distance L and which is pre-stored in the ROM 66, thereby determining a propagation distance L described later, and additionally substitutes the thus determined propagation distance L and the above-indicated actual pulse-wave propagation time DTa, with the following Expression 2, thereby determining an actual pulse-wave-propagation velocity PWVa (cm/sec) as the actual pulse-wave-propagation-velocity-related value:

$$L=\alpha t+\beta \quad \text{(Expression 1)}$$

($\alpha$ and $\beta$ are experimentally determined constants.)

$$PWVa=L/DTa \quad \text{(Expression 2)}$$

The thus determined actual pulse-wave-propagation-velocity-related value is displayed by the display device 70, together with the standard pulse-wave-propagation-velocity-related value determined by the standard-pulse-wave-propagation-velocity-related-value determining means 80 as described above. The propagation distance L obtained from the above Expression 1 is a difference between a distance (a length of the artery) between the aortic valve of the heart of the subject and a portion of the upper arm 12 around which the upper-arm cuff 20 is wound, and a distance (a length of artery) between the aortic valve of the heart of the subject and a portion of the ankle 16 around which the ankle cuff 42 is wound.

Figure 4:
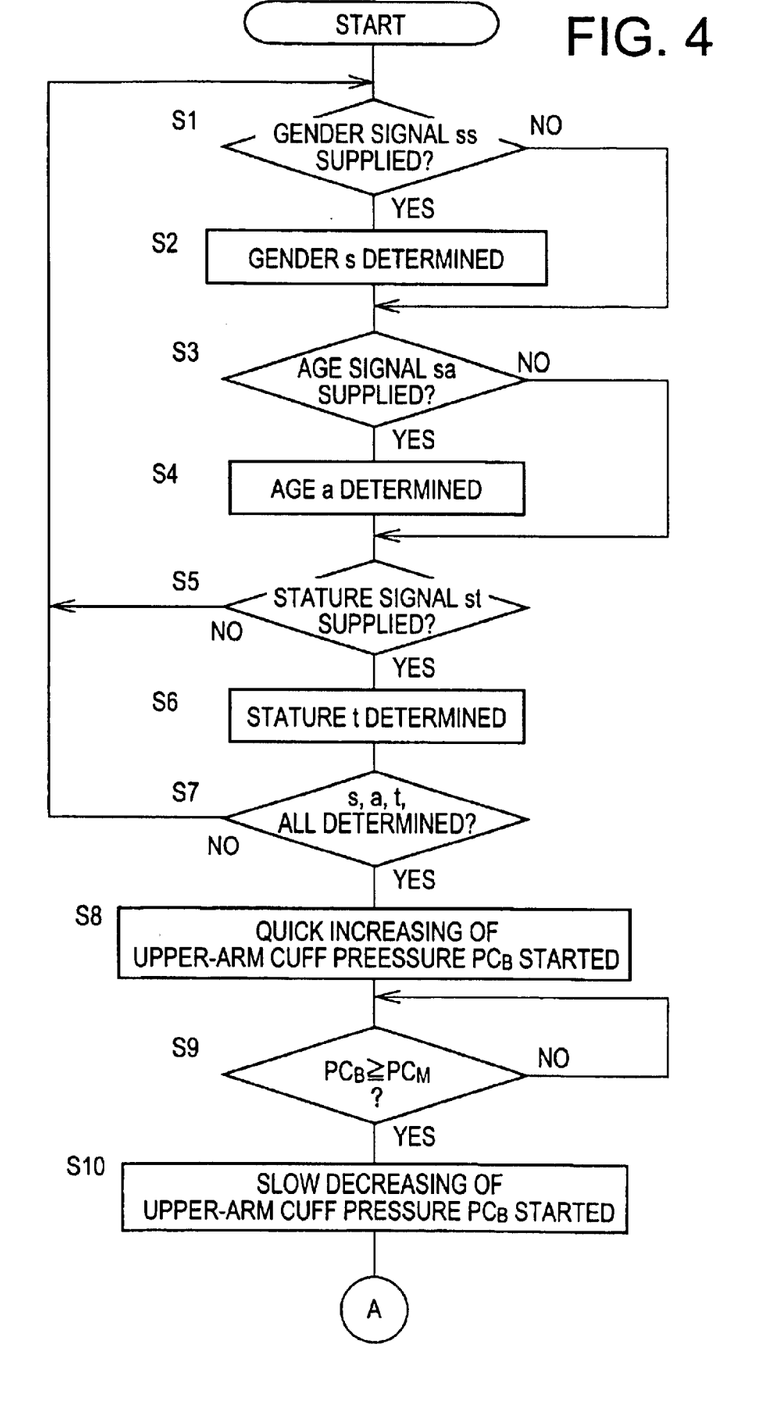
FIG. 4 is a flow chart representing a first portion of the essential control functions of the electronic control device, shown in FIG. 2.
Figure 5:
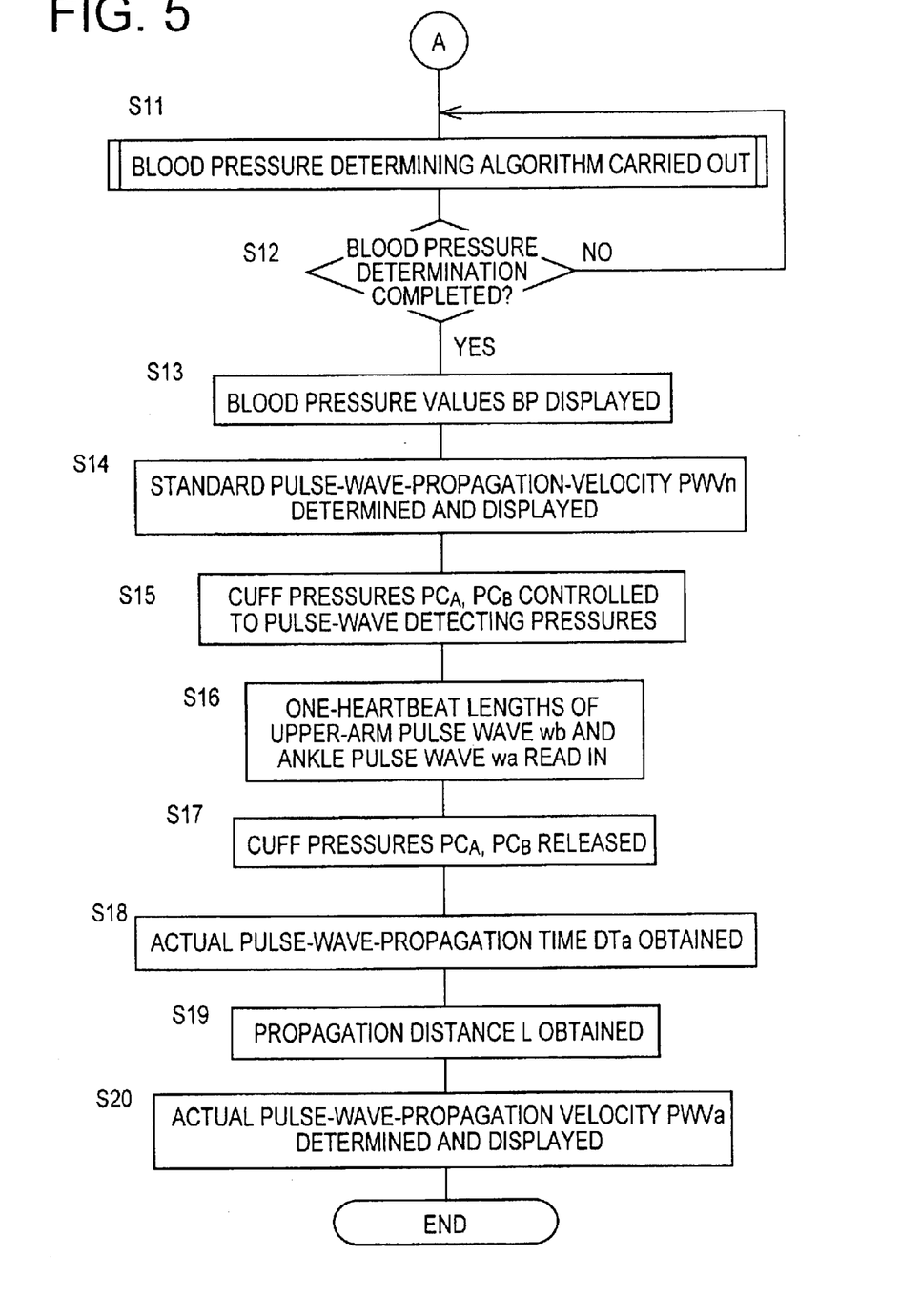
FIG. 5 is a flow chart representing a second portion of the essential control functions of the electronic control device, shown in FIG. 2.

FIGS. 4 and 5 are flow charts representing the essential control functions of the electronic control device 38, shown in FIG. 2. In the flow charts of FIGS. 4 and 5, the standard pulse-wave-propagation-velocity-determine relationships represented by the graphs of FIGS. 3A and 3B are used for determining the standard pulse-wave-propagation velocity.

In FIG. 4, at Step S1 through Step S 7 (hereinafter, "Step(s)" is omitted), the control device judges whether the gender s, the age a, and the stature t of the subject have been inputted through the input device 62. Described in detail, at S1, the control device judges whether the gender signal ss has been supplied from the input device 62. If a positive judgment is made at S1, the control flow goes to S2 to determine the gender s of the subject based on the supplied gender signal ss. S1 and S2 correspond to the gender determining means 76.

If a negative judgment is made at S1 or after S2 has been implemented, the control flow goes to S3 to judge whether the age signal sa has been supplied from the input device 76. If a positive judgment is made at S3, the control flow goes to S4 to determine the age a of the subject based on the supplied age signal sa. S3 and S4 correspond to the age determining means 78.

If a negative judgment is made at S3 or after S4 has been implemented, the control flow goes to S5 to judge whether the stature signal st has been supplied from the input device 62. If a positive judgment is made at S5, the control flow goes to S6 to determine the stature t of the subject based on the supplied stature signal st. If a negative judgment is made at S5, the control device repeats S1 and the following steps.

Then, at S7, the control device judges whether all of the gender s, age a, and stature t of the subject have been determined. If a negative judgment is made at S7, the control device repeats S1 and the following steps. If a positive judgment is made at S7, the control flow goes to S8 and the following steps to measure the blood pressure BP of the upper arm 12 of the subject.

Described in detail, at S8, the control device drives the air pump 30 and operates the pressure control valve 26, so as to start quickly increasing the upper-arm cuff pressure $PC_B$. Subsequently, at S9, the control device judges whether the upperarm cuff pressure $PC_B$ is equal to or higher than a predetermined target pressure value $PC_M$ (i.e., 180 mm/Hg). If a negative judgment is made at S9, the control device repeats this step and continues increasing the upper-arm cuff pressure $PC_B$. If a positive judgment is made at S9, the control flow goes to S10 to stop the air pump 30 and operate the pressure control valve 26 so as to slowly decrease the upper-arm cuff pressure $PC_B$ at a rate of about 3 mmHg/sec.

Next, there will be explained S11 and the following steps shown in the flow chart of FIG. 5. The control device implements S11 through S13 corresponding to the blood pressure determining means 74. Described more specifically, at S11, a systolic blood pressure value $BP_{SYS}$, a mean blood pressure value $BP_{MEAN}$, and a diastolic blood pressure value $BP_{DIA}$ are determined according to a well known oscillometric BP determining algorithm, based on the variation of respective amplitudes of pulses of the upper-arm pulse wave wb represented by the upper-arm-pulse-wave signal $SM_B$ successively obtained while the upper-arm cuff pressure $PC_B$ is slowly decreased at the rate of about 3 mmHg/sec. Then, at S12, the control device judges whether the measurement of blood pressure values has completed. Since the diastolic blood pressure value $BP_{DIA}$ is last determined during the slow decreasing of the upper-arm cuff pressure $PC_B$, the control device judges, at S12, whether the diastolic blood pressure value $BP_{DIA}$ has been determined. If a negative judgment is made at S12, the control device repeats S11 and the following steps to continue the BP determining algorithm. In the meantime, if a positive judgment is made at S12, the control flow goes to S13 to operate the display device 70 to display the determined systolic blood pressure value $BP_{SYS}$, mean blood pressure value $BP_{MEAN}$, and diastolic blood pressure value $BP_{DIA}$.

Then, the control flow goes to S14 corresponding to the standard-pulse-wave-propagation-velocity-related-value determining means 80. The control device selects one of a plurality of relationships between (A) (a2) age and (B) standard pulse-wave-propagation velocity, shown in the graphs of FIGS. 3A and 3B, based on the gender determined at S2 and the systolic blood-pressure value $BP_{SYS}$ determined at S1. Then, the control device determines a standard pulse-wave-propagation velocity PWVn, based on the age a determined at S4, according to the selected relationship, and controls the display device 70 to display the determined standard pulse-wave-propagation velocity PWVn. For instance, where the gender s of the subject determined at S2 is female and the systolic blood-pressure value $BP_{SYS}$ determined at S1 is 155 mmHg, the control device selects one of the plurality of predetermined relationships shown in FIGS. 3A and 3B, the selected relationship being represented by the following Expression 3, for instance:

Then, at S15, the control device controls the air pumps 30, 48 and the pressure control valves 26, 46 so as to change and keep the upper-arm cuff pressure $PC_B$ and the ankle cuff pressure $PC_A$ to and at the respectively predetermined pulse-wave detecting pressures, i.e., 50 mm/Hg.

S15 is followed by S16 at which the control device reads in respective one-heartbeat lengths of the upper-arm-pulse-wave signal $SM_B$ supplied from the pulse-wave filter circuit 34 and the ankle-pulse-wave signal $SM_A$ supplied from the pulse-wave filter circuit 52. Thereafter, the control flow goes to S17 to stop the air pumps 30, 48 and operate the pressure control valves 26, 46 so as to release the upper-ram cuff pressure $PC_B$ and ankle cuff pressure $PC_A$ to an atmospheric pressure. In the flow charts shown in FIGS. 4 and 5, S8 to S10 and S17 correspond to the cuff-pressure changing means 72.

Then, at S18, the control device determines respective rising points of the upper-arm pulse wave wb and the ankle pulse wave wa represented by the respective one-heartbeat-length signals $SM_B$ and $SM_A$ read in at S16. In addition, the control device determines, as an actual pulse-wave propagation time DTa, a time difference between a time of detection of the rising point of the upper-arm pulse wave wb and a time of detection of the rising point of the ankle pulse wave wa. Then, at S19, the control device substitutes the subject's stature t determined at S6, with the above-indicated Expression 1, thereby determining a propagation distance L. S19 is followed by S20 to substitute the actual pulse-wave-propagation time DTa determined at S18 and the propagation distance L determined at S19, with the above-indicated Expression 2, thereby determining an actual pulse-wave-propagation velocity PWVa, and control the display device 70 to display the determined actual pulse-wave-propagation velocity PWVa. In the flow charts shown in FIGS. 4 and 5, S16, and S18 to S20 correspond to the actual-pulse-wave-propagation-velocity-related-value determining means 82.

For instance, in a case where the actual pulse-wave-propagation velocity PWVa determined for the above-indicated 58-year-old female subject and displayed by the display device 70 at S20 is 1,850 cm/s, the subject is diagnosed as arteriosclerosis since the actual pulse-wave-propagation velocity PWVa (1,850 cm/sec) is significantly higher than the standard pulse-wave-propagation velocity (1,593 cm/sec) determined for the subject and displayed by the display device 70 at S14. Moreover, the systolic blood-pressure value $BP_{SYS}$ of the subject (155 mmHg) is relatively high, so that the subject is diagnosed as hypertension. In this case, administration of antihypertensive drug to the subject is started in order to lower the BP value.

Suppose that the actual pulse-wave-propagation velocity PWVa and the systolic blood pressure value $BP_{SYS}$ measured for the female subject several weeks after the initiation of administration of antihypertensive drug were 1,600 cm/s and 128 mmHg, respectively. In this case, it can be judged that the BP value of the subject is lowered to fall within a normal range. The actual pulse-wave-propagation velocity PWVa, however, is changed by not only a decrease of the degree of arteriosclerosis, but also a decrease of the blood pressure. Accordingly, it is difficult to judge to what extent the degree of arteriosclerosis has been lowered, based only on the actual pulse-wave-propagation velocity PWVa and the systolic blood pressure value $BP_{SYS}$. In the present pulse-wave-propagation-velocity-related-value obtaining apparatus 10, however, the standard pulse-wave-propagation velocity PWVn for the subject is displayed by the display device 70. For instance, the standard pulse-wave-propagation-velocity PWVn for the 58-year-old female subject whose systolic blood pressure value $BP_{SYS}$ is 128 mm/Hg is determined to be 1,332 cm/s, according to a selected one of the plurality of standard-pulse-wave-propagation-velocity-determine relationships shown in the graphs of FIGS. 3A and 3B. The determined standard pulse-wave-propagation velocity PWVn is displayed by the display device 70, so that it can be judged, by comparing the standard pulse-wave-propagation velocity PWVn and the actual pulse-wave-propagation velocity PWVa with each other, that the subject still needs to receive medical treatment to lower the degree of arteriosclerosis.

In the embodiment employing the flow charts of FIGS. 4 and 5, at S16, and S18 to S20 (corresponding to the standard pulse-wave-propagation-velocity-related-value determining means 82), the control device determines the standard pulse-wave-propagation velocity PWVn for a subject, according to the predetermined relationship between (A) (a1) blood pressure and (a2) age and (B) standard pulse-wave-propagation velocity PWVn, based on the age a and the systolic blood pressure $BP_{SYS}$ of the subject. This arrangement permits an accurate determination of the standard pulse-wave-propagation velocity PWVn.

In the embodiment employing the flow charts of FIGS. 4 and 5, the above-described predetermined relationship comprises two predetermined relationships between (A)(a1) blood pressure and (a2) age and (B) standard pulse-wave-propagation-velocity-related value that correspond to male and female, respectively. According to this arrangement, the standard pulse-wave-propagation-velocity-related value for a subject is determined by considering the gender s of the subject, in addition to the age a and the systolic blood pressure value $BP_{SYS}$ of the subject. Thus, a more accurate standard pulse-wave-propagation velocity PWVn can be determined.

In the embodiment employing the flow charts of FIGS. 4 and 5, the standard pulse-wave-propagation velocity PWVn and the actual pulse-wave-propagation velocity PWVa are both displayed by the display device 70, whereby it is easy to diagnose the degree of arteriosclerosis by comparison between the two values PWVn and PWVa.

While the present invention has been described in its embodiment by reference to the drawings, it is to be understood that the invention may otherwise be embodied.

For example, the illustrated apparatus 10 determines a standard pulse-wave-propagation-velocity-related value and measures an actual pulse-wave-propagation-related value. Since the actual pulse-wave-propagation-velocity-related value can be measured by a conventional apparatus, the present apparatus may be modified to determine only the standard pulse-wave-propagation-velocity-related value.

In the illustrated embodiment, the blood pressure determining means 74 determines the actual blood pressure BP of the upper arm 12 of the subject using the upper-arm cuff 20. The blood pressure BP which was measured by using other device may be inputted through the input device 62 to the present apparatus 10.

In the illustrated embodiment, the gender is determined by the gender determining means 76 based on the signal inputted through the input device 62. The gender of the subject may be automatically judged by the gender determining means 76 based on an image of a face or a voice of the subject. While the age of the subject is determined by the age determining means 78 based on the signal inputted through the input device 62, the age may be determined as a physiological age determined by analysis of a waveform of a pulse wave of the subject.

In the illustrated embodiment, the pre-determined relationship between (A)(a1) blood pressure and (a2) age and (B) standard pulse-wave-propagation-velocity-related value comprises two pre-determined relationships that correspond to male and female, respectively. The relationship may be predetermined without taking into account the gender of a subject. In the illustrated embodiment, the plurality of relationships shown in the graphs of FIGS. 3A and 3B are represented by the respective linear expressions of first order. A part of, or the entirety of, the plurality of linear expressions of first order may be replaced with expressions of second or higher order, or exponential or logarithmic expressions. Further, each predetermined relationship may be expressed in the form of a map which defines a relationship between (A) (a2) age and (B) standard pulse-wave-propagation-velocity-related value.

The illustrated pulse-wave-propagation-velocity-related-information obtaining apparatus 10 obtains the actual pulse-wave-propagation-velocity-related value with respect to the upper arm 12 and the ankle 16. At least one of the upper arm 12 and the ankle 16 may be replaced with a neck, a wrist or a femoral portion of the subject.

It is to be understood that the present invention may be embodied with other changes, improvements and modifications that may occur to a person skilled in the art without departing from the spirit and scope of the invention defined in the appended claims.

What is claimed is:

1. An apparatus for determining a standard pulse-wave-propagation-velocity-related value for a living subject, comprising:
    a blood-pressure measuring device for measuring a blood pressure of the subject;
    an age determining device for determining an age of the subject;
    a standard-pulse-wave-propagation-velocity-related-value determining device for determining the standard pulse-wave-propagation-velocity-related value for the subject, based on the blood pressure of the subject measured by the blood-pressure measuring device and the age of the subject determined by the age determining device, according to a predetermined relationship between (A) (a1) blood pressure and (a2) age and (B) standard pulse-wave-propagation-velocity-related value; and
    a gender determining device for determining a gender of the subject,
    wherein the predetermined relationship between (A)(a1) blood pressure and (a2) age and (B) standard pulse-wave-propagation-velocity-related value comprises two predetermined relationships between (A)(a1) blood pressure and (a2) age and (B) standard pulse-wave-propagation-velocity-related value that correspond to male and female, respectively, and
    wherein the standard-pulse-wave-propagation-velocity-related-value determining device determines the standard pulse-wave-propagation-velocity-related value for the subject, according to one of the two predetermined relationships between (A)(a1) blood pressure and (a2) age and (B) standard pulse-wave-propagation-velocity-related value that corresponds to the gender of the subject determined by the sender determining device.

2. An apparatus according to claim 1, further comprising:
    an input device operable for inputting the gender of the subject, wherein the gender determining device determines, as the gender of the subject, the gender inputted through the input device.

3. An apparatus for obtaining a pulse-wave-propagation-velocity-related value for a living subject, comprising:
    a standard-pulse-wave-propagation-velocity-related-value determining device according to claim 1;
    an actual-pulse-wave-propagation-velocity-related-value measuring device for measuring an actual pulse-wave-propagation-velocity-related value that is related to a velocity at which a pulse wave propagates in the subject; and
    a display device which displays the standard pulse-wave-propagation-velocity-related value determined by the standard-pulse-wave-propagation-velocity-related-value determining device and the actual pulse-wave-propagation-velocity-related value measured by the actual-pulse-wave-propagation-velocity-related-value measuring device.

4. An apparatus according to claim 3, wherein the actual-pulse-wave-propagation-velocity-related-value measuring device comprises:
    an upper-arm-pulse-wave detecting device which includes an upper-arm cuff adapted to be wound around an upper arm of the subject and detects an upper-arm pulse wave of the subject;
    an ankle-pulse-wave detecting device which includes an ankle cuff adapted to be wound around an ankle of the subject and detects an ankle pulse wave of the subject; and
    wherein the actual pulse-wave-propagation-velocity-related value measuring device measures the actual pulse wave propagation velocity related value based on the upper-arm pulse wave detected by the upper-arm-pulse-wave detecting device and the ankle pulse wave detected by the ankle-pulse-wave detecting device.

5. An apparatus according to claim 4, wherein the actual-pulse-wave-propagation-velocity-related-value measuring device comprises an actual-pulse-wave-propagation-time determining device for determining an actual pulse-wave-propagation time as a time difference between a time of detection of a prescribed point of the upper-arm pulse wave and a time of detection of a corresponding prescribed point of the ankle pulse wave.

6. An apparatus according to claim 5, wherein the actual-pulse-wave-propagation-velocity-related-value measuring device further comprises:

an actual-pulse-wave-propagation-velocity determining device for determining an actual pulse-wave-propagation velocity at which the pulse wave propagates, by dividing a propagation distance which is a difference between a distance between an aortic valve of the heart of the subject and a portion of the upper arm around which the upper-arm cuff is wound, and a distance between the aortic valve of the heart of the subject and a portion of the ankle around which the ankle cuff is wound, by the actual pulse-wave-propagation time determined by the actual-pulse-wave-propagation-time determining device.

7. An apparatus according to claim 1, further comprising:

an input device operable for inputting the age of the subject, wherein the age determining device determines, as the age of the subject, the age inputted through the input device.

* * * * *